United States Patent [19]

Umezawa et al.

[11] 4,439,603

[45] Mar. 27, 1984

[54] ANTHRACYCLINE DERIVATIVES OF β-RHODOMYCINONE GLYCOSIDES

[75] Inventors: Hamao Umezawa; Tomio Takeuchi, both of Tokyo; Tomoyuki Ishikura, Chigasaki; Akihiro Yoshimoto; Yasue Matsuzawa, both of Fujisawa; Yukio Takatsuki, Yokohama, all of Japan

[73] Assignee: Sanraku-Ocean Co., Ltd., Tokyo, Japan

[21] Appl. No.: 436,630

[22] Filed: Oct. 25, 1982

[30] Foreign Application Priority Data

Oct. 29, 1981 [JP] Japan ............................. 56-173465

[51] Int. Cl.³ ........................................... C07H 15/24
[52] U.S. Cl. ..................................... 536/6.4; 424/180
[58] Field of Search .................................... 536/6.4

[56] References Cited

U.S. PATENT DOCUMENTS

| | | | |
|---|---|---|---|
| 4,207,313 | 6/1980 | Umezawa et al. | 536/6.4 |
| 4,316,011 | 2/1982 | Oki et al. | 536/6.4 |
| 4,373,094 | 2/1983 | Oki et al. | 536/6.4 |

*Primary Examiner*—Johnnie R. Brown
*Attorney, Agent, or Firm*—James J. Ralabate

[57] ABSTRACT

New anthracycline derivatives, β-rhodomycinone-RDA, β-rhodomycinone-RDRs and β-rhodomycinone-RD having potent anticancer activities and lower toxicities and a process for the production thereof by reduction or hydrolysis of β-rhodomycinone-RDC are disclosed.

3 Claims, No Drawings

ANTHRACYCLINE DERIVATIVES OF β-RHODOMYCINONE GLYCOSIDES

BACKGROUND OF THE INVENTION (1) Field of the Invention

The present invention relates to new anthracycline derivatives and a process for their preparation. More particularly, the present invention relates to new anthracycline derivatives, β-rhodomycinone-RDA, β-rhodomycinone-RDRs and β-rhodomycinone-RD, to the process for the preparation thereof by reduction or acid hydrolysis of β-rhodomycinone-RDC and to the methods for their recovery and purification.

(2) Description of the Prior Art

A number of anthracycline glycosides have been found in the culture medium of Streptomyces, and are desribed in prior literatures. Among them, daunomycin and adriamycin have already been clinically applied to human cancers.

Rhodomycinones, iso-rhodomycinone and rhodomycin-related antibiotics are described in Chem. Ber. 88, 1792–1818 (1955); Chem. Ber. 101, 1341–1348 (1968); J. Med. Chem., 20, 957–960 (1977); Pharmacie 27, 782–789 (1972); Zeit. Allg. Mikrobiol., 14, 551–558 (1974); Tetrahed. Lett. No. 38, 3699–3702 (1973); Folia Microbiol., 24, 293–295 (1979) and J. Antibiotics, 32, 420 (1979).

Aclacinomycin A is disclosed in U.S. Pat. No. 3,988,315 and by Oki et al. in J. Antibiotics 28, 830 (1975) and 32, 791–812 (1979).

Cinerubins A and B are disclosed in U.K. Pat. No. 846,130, U.S. Pat. No. 3,864,480, Keller-Schierlein et al., "Antimicrobial Agents and Chemotherapy", page 68 (1970), Chemical Abstracts 54, 1466i (1960) and J. Antibiotics 28, 830 (1975).

Further illustrative and summary disclosures of anthracycline antibiotics can be located in the Index of Antiobiotics from Actinomycetes, Hamao Umezawa, Editor-in-Chief, University Park Press, State College, Pa., U.S.A. (1967) as follows:

| Antibiotics | Page Numbers |
|---|---|
| Aclacinomycins A and B | 101–102 |
| Adriamycin | 122 |
| Carminomycin I | 225 |
| Galirubins S - D | 405–408 |
| Rhodomycins X - Y | 879–880 |
| β-Rhodomycins | 881–885 |
| γ-Rhodomycins | 886–892 |
| Steffimycin | 945 |

The textbook, Antibiotics, Volume 1, Mechanism of Action, edited by David Gottlieb and Paul D. Shaw, Springer-Verlag New York, Inc., N.Y. (1967) at pages 190–210, contains a review by A. Dimarco entitled "Daunomycin and Related Antibiotics".

Information Bulletin, No. 10, International Center of Information of Antibiotics, in collaboration with WHO, December, 1972, Belgium, reviews anthracyclines and their derivatives.

Furthermore, new anthracycline glycoside derivatives of rhodomycin-group, ε-rhodomycin-RDC, ε-isorhodomycin-RDC, β-rhodomycin-RDC, γ-rhodomycin-RDC and β-pyrromycin-RDC and a process for the production thereof by microbiological conversion method are disclosed (U.S. Pat. No. 4,316,011).

DETAILED DESCRIPTION OF THE INVENTION

The present invention provides novel anthracycline derivatives, and relates to a process for the production thereof, and more particularly, the present invention relates to the novel anthracycline derivatives of the general formula I:

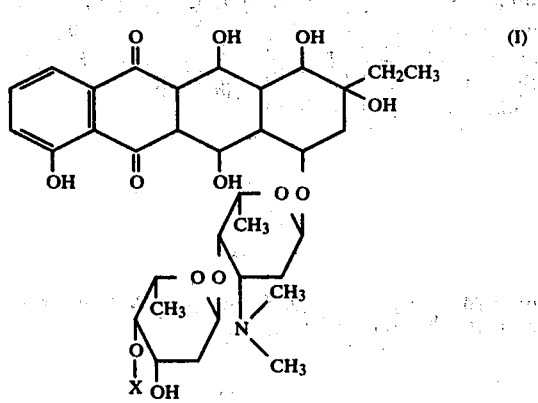

wherein X is a hydrogen atom or the following sugar chain moiety

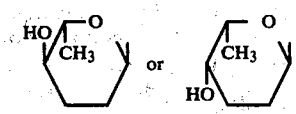

A new antitumor anthracycline antibiotic, β-rhodomycinone-RDC of the following formula II:

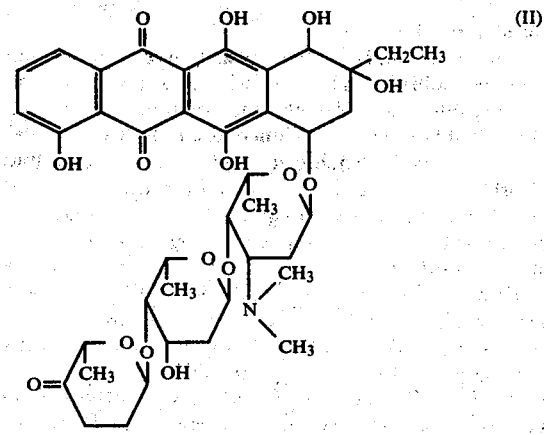

has been found by the present inventors and disclosed in U.S. Pat. No. 4,316,011 (wherein β-rhodomycinone-RDC is designated as β-rhodomycin-RDC).

It has been found that the compound of the formula I remarkably inhibits the growth and nucleic acids synthesis of cultured mouse leukemia L1210 cells at a low concentration and is possibly used as an antitumor agent, after a long intensive study to try to obtain much better antitumor substances than the above-mentioned antibiotic, β-rhodomycinone-RDC (wherein R is rhodosamine, D is 2-deoxy-fucose and C is cinerulose A).

The compounds of the present invention may be obtained by reduction or hydrolysis of the compound of the formula II or acid addition salts thereof, in which the reaction process is known per se.

For example, β-rhodomycinone-RDC of the formula II is treated with a reducing reagent such as sodium boron hydride or lithium aluminum hydride under appropriate reaction conditions to reduce the carbonyl group of the terminal sugar moiety, cinerulose A (in the present invention cinerulose A is shown as C). The sugar moiety is converted to amicetose (in the present invention amicetose is shown as A) or rhodinose (in the present invention rhodinose is shown as Rs) and β-rhodomycinone-RDA, wherein X of the general formula I is a group of the formula:

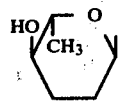

or β-rhodomycinone-RDRs, wherein X of the general formula I is a group of the formula:

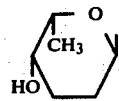

is obtained. Furthermore, β-rhodomycinone-RDC, β-rhodomycinone-RDA or β-rhodomycinone-RDRs is subjected to mild hydrolysis with 0.05–0.5 N hydrochloric acid or sulfuric acid to remove the terminal sugar, and β-rhodomycinone-RD, wherein X of the general formula I is a hydrogen atom, is obtained. The compounds of the general formula I thus obtained may be purified according to the known isolation and purification processes that are usually used in the art of anthracycline antibiotics.

The compounds of the present invention are basic and form addition salts with various kinds of inorganic and organic acids. Namely, the compounds of the general formula I may be obtained as addition salts with an acid such as hydrochloric acid, sulfuric acid, phosphoric acid, oxalic acid, nitric acid, acetic acid, propionic acid, maleic acid, oleic acid, palmitic acid, citric acid, succinic acid, tartaric acid, fumaric acid, glutamic acid, pantothenic acid, laurylsulfonic acid, benzenesulfonic acid and naphthalenesulfonic acid by the known processes for formation of salt from free bases. A representative process for salt formation consists of treating the compound of free base form of the present invention with the above-mentioned acid in an appropriate solvent and obtaining the reaction product by freeze-drying or recovering it by precipitation with a solvent in which the corresponding salt is rarely dissolved.

Physicochemical properties of the compounds of the present invention are given in Table 1.

TABLE 1

| compound | Physicochemical Properties | | |
|---|---|---|---|
| | β-rhodomy-cinone-RDA | β-rhodomy-cinone-RDRs | β-rhodomy-cinone-RD |
| Appearance | reddish powder | reddish powder | reddish powder |
| Molecular weight | 787.9 | 787.9 | 673.7 |
| Elementary analysis | as $C_{40}H_{53}NO_{15}$ | as $C_{40}H_{53}NO_{15}$ | as $C_{34}H_{43}NO_{13}$ |
| Observed | C 60.95 | C 60.94 | C 60.60 |
| | H 6.81 | H 6.80 | H 6.45 |

TABLE 1-continued

| compound | Physicochemical Properties | | |
|---|---|---|---|
| | β-rhodomy-cinone-RDA | β-rhodomy-cinone-RDRs | β-rhodomy-cinone-RD |
| Calculated | N 1.76 | N 1.77 | N 2.10 |
| | C 60.98 | C 60.98 | C 60.62 |
| | H 6.78 | H 6.78 | H 6.43 |
| | N 1.78 | N 1.78 | N 2.08 |
| Melting point (°C.) | 168–170° | 170–172° | 170–172° |
| Ultraviolet and visible absorption spectra $\lambda_{max}^{90\% MeOH}$ nm ($E_{1cm}^{1\%}$) | 235 (508) | 235 (510) | 235 (590) |
| | 252 (313) | 253 (303) | 253 (360) |
| | 295 (90) | 295 (93) | 292 (107) |
| | 497 (175) | 495 (187) | 496 (206) |
| | 530 (135) | 530 (137) | 530 (156) |
| | 580 (40) | 580 (26) | 580 (37) |
| Infrared absorption spectrum cm$^{-1}$ KBr tablet | 1600, 1020 | 1600, 1020 | 1600, 1015 |
| | 1010, 1000 | 1000, 975 | 1000, 990 |
| | 965 | | 965 |
| Rf values | | | |
| 1* | 0.07 | 0.07 | 0.02 |
| 2 | 0.62 | 0.58 | 0.40 |

*1: CHCl$_3$—MeOH (20:1)
 2: CHCl$_3$—MeOH—aqNH$_3$ (100:15:0.2)

Solubilities of the compounds of the present invention, β-rhodomycinone-RDA, -RDRs, and -RD are similar. They are soluble in acidic water, methanol, ethanol, n-butanol, acetone, ethyl acetate, chloroform, benzene, toluene, dimethylsulfoxide and methyl cellosolve, slightly soluble in water, ether and n-hexane. The color of the solutions, when they are dissolved, is red or reddish yellow, which is changed to violet in alkaline solution.

Chemical structures of the compounds of the present invention were determined by IR, UV, NMR and elementary analysis, and also by the instrumental analysis of the aglycones and sugars that are formed by the hydrolysis with acid of the compounds of the present invention. Namely, IR absorption spectra showed absorption peaks of hydrogen bond-type quinone carbonyl group at 1600 cm$^{-1}$ and sugar ether group at 965–1020 cm$^{-1}$. The present compounds were confirmed to have the same chromophore as β-rhodomycinone-RDC (U.S. Pat. No. 4,316,011) has, because they have a maximum absorption at 495–497 nm in the visible absorption spectra. β-Rhodomycinone-RDA, -RDRs and -RD were each dissolved in 0.1 N hydrochloric acid and heated at 85° C. for 30 minutes. Each aglycone thus formed was isolated, and the IR, UV, NMR, and Mass spectra, and melting point were measured. The values were in accordance with those of β-rhodomycinone (Chem. Ber., 96, 1359 (1963) and 101, 1341 (1968)), which assures that the compounds of the present invention have the same aglycone as β-rhodomycinone-RDC.

The sugar moieties of the compounds of the present invention were analized by silica gel thin-layer chromatography (Merck Co. 60F$_{254}$, Solvent system; n-butanol: acetic acid:water, 4:1:1) with the neutralized and concentrated water-soluble fraction of the hydrolysate. β-Rhodomycinone-RDA and -RDRs gave three kinds of sugars, and β-rhodomycinone-RD provided two kinds of sugars.

Comparison of these sugars with authentic sugar samples obtained from MA144 M1 and MA144 N1 (J. Antibiotics 32, 801–819, 1979) showed that 3 kinds of sugars from β-rhodomycinone-RDA were amicetose, 2-deoxyfucose and rhodosamine, that 3 kinds of sugars from β-rhodomycinone-RDRs were rhodinose, 2-deoxy-fucose and rhodosamine, and that two kinds of sugars from β-rhodomycinone-RD were 2-deoxyfucose and rhodosamine.

Accordingly, it has been found that the compounds of the present invention are novel substances having the structure of the formula I which are chemically derived from the new anthracycline antibiotic, β-rhodomycinone-RDC.

Low concentrations of the compounds of the present invention remarkably inhibited the growth and nucleic acids synthesis of cultured mouse leukemia L1210 cells. The L1210 cells were cultivated at 37° C. overnight and transferred to RPMI (Roswell Park Memorial Institute) 1640 medium containing 20% calf serum at their exponential growth phase so as to give a cell concentration of $4 \times 10^4$ cells/ml. The compounds of the present invention were added to the medium at a concentration of 0.01–0.25 μg/ml. Incubation was performed in a $CO_2$-incubator at 37° C. for 2 days and then the number of viable cells was counted.

Independently of the above-mentioned experiment, the compounds of the present invention were added to an about $5 \times 10^5$ cells/ml L1210 cell suspension in RPMI 1640 medium containing 10% calf serum at a concentration of 0.02–2.5 μg/ml. After 15 minutes, $^{14}$C-uridine (0.05 μCi/ml) or $^{14}$C-thymidine (0.05 μCi/ml) was added to the suspension and pulse-labeling was carried out at 37° C. for 60 minutes. The reaction was stopped by addition of a cold 10% trichloroacetic acid solution and an acid-insoluble fraction was precipitated. The precipitate was washed with a cold 5% trichloroacetic acid and the radioactivity was measured. Table 2 shows the concentrations of 50% inhibition for cell growth and for incorporation of radioactivity on the basis of the control value.

TABLE 2

| | Antitumor Activity 50% Inhibitory concentration (μg/ml) | | |
|---|---|---|---|
| compound | Growth inhibition after 48 hours | $^{14}$C-Thymidine (Inhibition of DNA synthesis) | $^{14}$C-Uridine (Inhibition of RNA synthesis) |
| β-Rhodomycinone-RDA | 0.028 | 0.52 | 0.095 |
| β-Rhodomycinone-RDRs | 0.016 | 0.54 | 0.085 |
| β-Rhodomycinone-RD | 0.01 | 0.36 | 0.13 |
| β-Rhodomycinone-RDC | 0.01 | 0.45 | 0.07 |

Accordingly, it has been found that the novel compounds of the present invention, β-rhodomycinone-RDA, -RDRs and -RD, have an antitumor effect on L1210 leukemia cells. On the other hand, their acute toxicities ($LD_{50}$ values) against mice upon a single intraabdominal injection were 40.6, 35.3, and 25.5 mg/kg respectively.

β-Rhodomycinone-RDA, -RDRs and -RD having antitumor activity in the present invention can be administered in the form of suspension in distilled water or physiological saline water and the like. They can be administered parenterally by subcutaneous, intravenous or intramuscular injection, and can be administered in capsules orally. It will be appreciated that the actual preferred amounts will vary according to the particular compound being used, the mode of application and the particular situs and organism being treated. Many factors that modify the action of the drug will be taken into account by those skilled in the art, for example, age, body weight, sex, diet, time of administration, route of administration, rate of excretion, drug combinations, reaction sensitivities and severity of the disease. Optimal application rates for a given set of conditions can be ascertained by those skilled in the art using conventional dosage determination tests in view of the above guidelines.

The present invention is further illustrated by the following examples.

EXAMPLE 1

β-Rhodomycinone-RDC (1 g) was dissolved in 300 ml of chloroform and 45 ml of ethanol. To the solution, 100 mg of sodium boron hydride was added and the mixture was stirred at room temperature for 15 minutes. After the reaction was completed, 100 ml of chloroform and 100 ml of distilled water was added to decompose the excess of sodium boron hydride. The chloroform layer was washed with $10^{-2}$ M ethylene-diamine tetraacetate (EDTA), pH 7.0, and with distilled water twice, dried with anhydrous sodium sulfate, and then evaporated to dryness under reduced pressure. The residue obtained (540 mg) was spotted onto a silica gel plate for preparative layer chromatography (Merck Co. $PF_{254}$) in a linear manner. Development was carried out with a solvent system of chloroform:methanol (100:15, V/V). The silica gel layer at Rf 0.39 corresponding to β-rhodomycinone-RDA, and at Rf 0.32 corresponding to β-rhodomycinone-RDRs was peeled off. Each gel was treated with a mixture of chloroform:methanol:aqueous ammonia (100:15:0.2) for extraction. Precipitation with n-hexane from each concentrated extract provided 220 mg of β-rhodomycinone-RDA and 40 mg of β-rhodomycinone-RDRs as reddish powder.

EXAMPLE 2

β-Rhodomycinone-RDA (200 mg) obtained according to Example 1 was dissolved in 200 ml of 0.05 N hydrochloric acid and hydrolyzed at room temperature for 2 hours. The hydrolysate was neutralized to pH 7.5 with diluted aqueous alkali solution and treated with 200 ml of chloroform for extraction 4 times. The chloroform extracts were combined, dried with anhydrous sodium sulfate, and then evaporated to dryness under reduced pressure. The residue obtained (160 mg) was subjected to preparative layer chromatography on a silica gel plate (solvent system; chloroform:methanol:aqueous ammonia, 60:10:0.1). The silica gel layer at Rf 0.42 corresponding to β-rhodomycinone-RD was peeled off and treated with a mixture of chloroform:methanol:aqueous ammonia (100:15:0.2) for extraction. The extract was concentrated and n-hexane was added to precipitate the extracted reaction product, and 50 mg of β-rhodomycinone-RD was obtained as reddish powder.

EXAMPLE 2

β-Rhodomycinone-RDRs (10 mg) obtained according to Example 1 was dissolved in 10 ml of 0.05 N hydrochloric acid and hydrolyzed at room temperature for one hour. The hydrolysate was neutralized to pH 7.5 with diluted aqueous alkali solution and treated with 20 ml of chloroform for extraction. The chloroform layers were combined, dried with anhydrous sodium sulfate, and evaporated to dryness in vacuo. The residue obtained (9 mg) was isolated and purified in the same manner as in Example 2. Three mg of β-rhodomycinone-RD was obtained as reddish powder.

EXAMPLE 4

β-Rhodomycinone-RDC (100 mg) was dissolved in 100 ml of 0.5 N hydrochloric acid and hydrolyzed at room temperature for 10 minutes. Nine mg of β-rhodomycinone-RD was obtained as reddish powder by the same isolation and purification procedure as described in Example 2.

What is claimed is:

1. Anthracycline derivatives having the formula

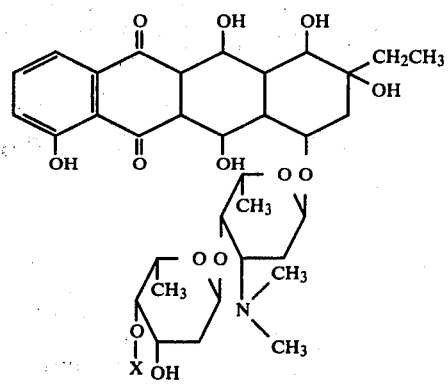

wherein X is the following sugar chain moiety

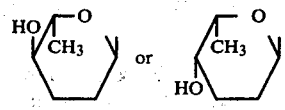

or a non-toxic acid addition salt thereof.

2. An anthracycline derivative and non-toxic acid addition salts thereof according to claim 1 in which the compound is β-rhodomycinone-RDA of the formula 1 wherein X is

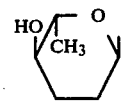

3. An anthracycline derivative and non-toxic acid addition salts thereof according to claim 1 in which the compound is β-rhodomycinone-RDRs of the formula 1 wherein X is

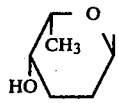

* * * * *

UNITED STATES PATENT AND TRADEMARK OFFICE
CERTIFICATE OF CORRECTION

PATENT NO. : 4,439,603

DATED : March 27, 1984

INVENTOR(S) : Hamao Umezawa et al

It is certified that error appears in the above-identified patent and that said Letters Patent is hereby corrected as shown below:

Column 2, lines 10-25, Formula I should appear as shown on the attached sheet.

Column 8, lines 1-15, Formula I should appear as shown on the attached sheet.

UNITED STATES PATENT AND TRADEMARK OFFICE
CERTIFICATE OF CORRECTION

PATENT NO. : 4,439,603

DATED : March 27, 1984

INVENTOR(S) : Hamao Umezawa et al

It is certified that error appears in the above-identified patent and that said Letters Patent is hereby corrected as shown below:

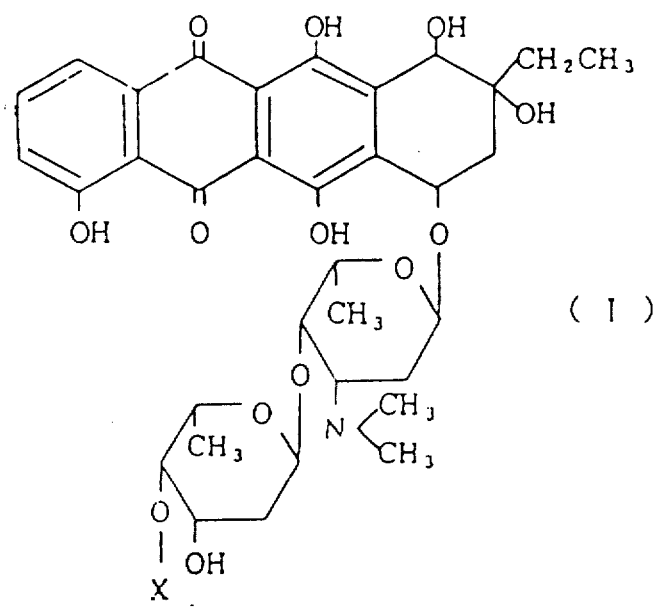

( I )

Signed and Sealed this

Second Day of October 1984

[SEAL]

Attest:

Attesting Officer

GERALD J. MOSSINGHOFF

Commissioner of Patents and Trademarks